(12) United States Patent
Fetzer et al.

(10) Patent No.: US 9,500,627 B2
(45) Date of Patent: Nov. 22, 2016

(54) METHOD FOR ULTRASONIC INSPECTION OF IRREGULAR AND VARIABLE SHAPES

(71) Applicant: The Boeing Company, Chicago, IL (US)

(72) Inventors: Barry Allen Fetzer, Renton, WA (US); James C. Kennedy, Renton, WA (US); Navpreet S. Grewal, Redmond, WA (US)

(73) Assignee: The Boeing Company, Chicago, IL (US)

( * ) Notice: Subject to any disclaimer, the term of this patent is extended or adjusted under 35 U.S.C. 154(b) by 456 days.

(21) Appl. No.: 14/100,042

(22) Filed: Dec. 9, 2013

(65) Prior Publication Data
US 2014/0095085 A1    Apr. 3, 2014

Related U.S. Application Data

(63) Continuation-in-part of application No. 13/532,815, filed on Jun. 26, 2012, now Pat. No. 9,366,655.

(51) Int. Cl.
*G01N 29/24* (2006.01)
*G01N 29/265* (2006.01)
(Continued)

(52) U.S. Cl.
CPC .......... *G01N 29/262* (2013.01); *G01N 29/043* (2013.01); *G01N 29/11* (2013.01); *G01N 29/225* (2013.01); *G01N 2291/2638* (2013.01); *G01N 2291/2694* (2013.01)

(58) Field of Classification Search
CPC .... G01N 29/11; G01N 29/06; G01N 29/069; G01N 29/34; G01N 29/341; G01N 29/343; G01N 29/346; G01N 29/4409; G01N 29/4427; G01N 29/48; G01N 29/262; G01N 2291/2638

USPC ........ 73/602, 633, 640, 641, 621, 625, 626, 73/628

See application file for complete search history.

(56) References Cited

U.S. PATENT DOCUMENTS 4,848,159 A * 7/1989 Kennedy .............. G01N 29/265
73/588
6,722,202 B1    4/2004 Kennedy et al.
(Continued)

FOREIGN PATENT DOCUMENTS

DE    102008002450 A1 * 10/2009 ........... G01N 29/069

OTHER PUBLICATIONS

Meyer et al., "Ultrasonic Testing Using Phased Arrays", http://www.ndt.net/article/wcndt00/papers/idn151/idn151.htm, Oct. 2, 2013.
(Continued)

*Primary Examiner* — Laura Martin
*Assistant Examiner* — Rose M Miller
(74) *Attorney, Agent, or Firm* — Ostrager Chong Flaherty & Broitman P.C.

(57) ABSTRACT

A system and a method for enabling ultrasonic inspection of multiple or varying radii of a composite part without making mechanical adjustments to compensate for changes in the radius dimension. The system may comprise one or more ultrasonic pulser/receivers, one or more ultrasonic transducer arrays, a probe body or shoe to hold and position the array(s), ultrasonic data acquisition application software to drive the array(s), and ultrasonic data acquisition application software to select the best signal response for each column of pixels to be displayed. The inspection methodology enables the examination of smooth curved fillets which change shape along the length of the part.

20 Claims, 9 Drawing Sheets

(51) Int. Cl.
  *G01N 29/26* (2006.01)
  *G01N 29/11* (2006.01)
  *G01N 29/04* (2006.01)
  *G01N 29/22* (2006.01)

(56) References Cited

U.S. PATENT DOCUMENTS

| | | |
|---|---|---|
| 6,789,427 B2 | 9/2004 | Batzinger et al. |
| 6,993,971 B2 | 2/2006 | Bossi et al. |
| 7,231,826 B2 | 6/2007 | Bossi et al. |
| 7,337,673 B2 | 3/2008 | Kennedy et al. |
| 7,484,413 B2 | 2/2009 | Georgeson et al. |
| 8,082,793 B2 | 12/2011 | Sarr et al. |
| 2008/0121040 A1* | 5/2008 | MacLauchlan ...... G01N 29/265 73/618 |
| 2010/0094606 A1* | 4/2010 | Richard ................. G01B 17/06 703/2 |
| 2011/0100128 A1* | 5/2011 | Bond-Thorley ....... G01N 29/28 73/641 |
| 2013/0020144 A1 | 1/2013 | Troy et al. |
| 2013/0197824 A1* | 8/2013 | Baba ...................... G01N 29/04 702/39 |
| 2013/0239689 A1* | 9/2013 | Bbond-Thor ........ G01N 29/221 73/625 |
| 2013/0298682 A1 | 11/2013 | Motzer et al. |
| 2014/0051970 A1* | 2/2014 | Ebisawa ............. G01S 7/52047 600/407 |

OTHER PUBLICATIONS

Habermehl et al., "Ultrasonic Phased Array Tools for Composite Inspection During Maintenance and Manufacturing," 17th World Conf. on Nondestructive Testing, Oct. 25-28, 2008, Shanghai, China.

* cited by examiner

METHOD FOR ULTRASONIC INSPECTION OF IRREGULAR AND VARIABLE SHAPES

RELATED PATENT APPLICATION

This application is a continuation-in-part of and claims priority from U.S. patent application Ser. No. 13/532,815 filed on Jun. 26, 2012.

BACKGROUND

This disclosure generally relates to inspection equipment and methods, and deals more particularly with methods and apparatus for inspecting structures having irregular and variable shapes, especially soft-tooled structures made of composite material.

A variety of elongated composite structures may have relatively confined internal cavities that require inspection in order to assure that the structure meets production and/or performance specifications. The composite radii formed using tooling are not always well defined and may vary from part to part. In some cases, dimensional or contour variations may make reliable inspection using conventional methods more challenging. In view of the deviation from circularity of tooled composite radii, the term "radius" as used hereinafter should be construed non-strictly to include circular profiles and curved profiles which deviate from circularity.

The desire to maximize performance and minimize weight in commercial aircraft has resulted in designs with varying radii that may be implemented in either hard or soft tooling. Soft tooling produces inspection surfaces that vary in an unpredictable manner, within limits, but beyond the tolerance limits of fixed-probe ultrasonic inspection methods. Designed radius changes also vary beyond the limits of fixed-probe methods. New low-turbulence aerodynamic shapes present continuously changing complex surfaces for inspection. Existing fixed probes are not capable of inspecting some surfaces.

The foregoing design methodology creates part structures whose radius dimensions vary along the length of the part. There are also a vast amount of individual composite parts with unique radius dimensions. Whether inspecting multiple parts with many radii or a single part with multiple radii, operators consume large amounts of time to adjust their probes to the different radius dimensions. In addition, the designers of the non-destructive inspection (NDI) systems have to design and fabricate unique probes for the variety of radius shapes.

In particular cases the problem can be solved by using several fixed probes, by using a probe that is manually adjustable or by using a probe that automatically mechanically adjusts during probe scanning. Operators have to adjust the probe while inspecting multiple radii or varying radii. The distance between the radius array probe and the composite radii structure dictates the signal integrity while performing an ultrasonic inspection. One method is to align the ultrasonic probe on a concentric circle with respect to the part radii. Should the radius of the part change, the position of the probe would also need to change.

An NDI system capable of inspecting multiple or varying radii without mechanically adjusting for changes in the radius dimension would be useful.

SUMMARY

The system and method disclosed herein enable the ultrasonic inspection of multiple or varying radii of a composite part without making mechanical adjustments to compensate for changes in the radius dimension. In accordance with some embodiments, the system comprises one or more ultrasonic pulser/receivers, one or more ultrasonic transducer arrays, a probe body or shoe to hold and position the array(s), ultrasonic data acquisition application software to drive the array(s), and ultrasonic data acquisition application software to select the best signal response for each column of pixels to be displayed. The inspection methodology is based on the assumption that the different radii to be inspected are smooth curves which change shape smoothly along the length of the part. One target application is composite parts having smooth-curve fillet radii, such as wing panel stringers, wing box spars, fuselage stringers, frames, floor beams, shear ties, etc.

In accordance with the embodiments disclosed in detail hereinafter, the ultrasonic transducer array is pulsed with a large number of beams to provide inspection for a family of surfaces, represented by respective cross-sectional curves and covering the range of possibilities for the unknown shape. Each curve, regardless of length, is populated with the same number of inspection points, which after numbering, define groups of associated points, which groups can be placed in one-to-one correspondence with columns of display pixels, thereby enabling the points to be mapped unambiguously to the display pixels. The data is processed by selecting only those beams that provide the largest echo for a given point group. The echo can be from the part surface or from the interior.

Instead of mechanically adjusting a probe, multiple wavefronts are created by a computer-controlled ultrasonic transducer array to accommodate different radius dimensions and shapes of a composite part. These multiple wavefronts are adjusted using ultrasonic beamforming application software and later the best resulting wavefront is selected using ultrasonic data analysis application software. The transmission of multiple sets of ultrasound beams for inspecting radii of differing radius dimension and shape is done electronically by phasing the elements in the transducer array(s) to cover the expected (i.e., predicted) surface of the part as well as the full range of radius variability. The phasing is done in accordance with predetermined focal laws. (As used herein, the term "focal laws" refers to the programmed pattern of time delays applied to pulses and outputs of individual transducer elements during formation of transmit and receive beams.) The ultrasonic data analysis application software then selects parameter data corresponding to the best receive beam for each spatial element of the part for displaying a characteristic thereof (e.g., amplitude) as a pixel and discards parameter data for other receive beams.

One aspect of the subject matter disclosed in detail herein is a system for scanning a radius of a part comprising: an array of transducer elements; a probe body that holds the array of transducer elements; and a pulser/receiver unit programmed to perform the following operations: (a) pulsing transducer elements of the array in accordance with a first set of focal laws to emit a first plurality of beams in sequence, the beams of the first plurality being respectively directed normal to a first plurality of target locations located on respective curved line segments; (b) after each beam of the first plurality of beams is emitted, processing transducer output signals from the transducer elements in accordance with a second set of focal laws to derive a first set of parameter values characterizing the strengths of the respective echoes received from the first plurality of target locations; (c) pulsing transducer elements of the array in accordance with a third set of focal laws to emit a second plurality of beams in sequence, the beams of the second plurality being respectively directed normal to a second plurality of target locations located on the respective curved line segments; and (d) after each beam of the second plurality of beams is emitted, processing transducer output signals from the transducer elements in accordance with a fourth set of focal laws to derive a second set of parameter values characterizing the strength of the respective echoes received from the second plurality of target locations. The first and second pluralities of target locations are respectively located along a plurality of curved line segments which span an expected total range of variation of a radius surface of a part to be inspected.

The system described in the preceding paragraph further comprises a display unit comprising rows and columns of pixels and a computer system programmed to perform the following operations: (e) selecting one of the first set of parameter values that satisfies a condition; (f) selecting one of the second set of parameter values that satisfies the condition; (g) controlling the display unit to display in a first pixel a first pixel value which is a function of at least the parameter value selected in operation (e); and (h) controlling the display unit to display in a second pixel a second pixel value which is a function of at least the parameter value selected in operation (f). The first and second pixels are adjacent to each other and in the same column. In accordance with one embodiment, the parameter is amplitude and the condition is having the greatest amplitude.

Another aspect of the subject matter disclosed in detail hereinafter is a method for inspecting a radius of a part, comprising the following steps: (a) generating a cross-sectional model of a probe in contact with a part comprising first and second surfaces connected by a radius surface, the probe comprising an array of transducer elements, the cross-sectional model comprising first and second lines representing respective cross sections of the first and second surfaces and a plurality of curved line segments which span an expected total range of variation of a radius dimension of the radius surface of the part, each of the curved line segments terminating at the first and second lines; (b) calculating a first set of focal laws for controlling the transducer elements to emit a plurality of beams respectively directed normal to a first plurality of target locations respectively located on the curved line segments; (c) calculating a second set of focal laws which are designed to receive respective return signals representing respective echoes returned to the transducer elements from the first plurality of target locations; (d) placing the probe in a first position relative to the part, wherein the position of the probe relative to the part in a cross-sectional plane conforms to the relative position represented by the cross-sectional model; (e) pulsing the transducer elements of the array to transmit a first plurality of beams respectively directed normal to the first plurality of target locations in accordance with the first set of focal laws; (f) after each beam of the first plurality of beams is emitted, processing transducer output signals from the transducer elements in accordance with the second set of focal laws to derive a set of parameter values characterizing the strength of the respective echoes received from the first plurality of target locations; (g) selecting one of the set of parameter values that satisfies a condition; and (h) displaying a pixel value which is a function of at least the parameter value selected in step (g). In the embodiments disclosed herein, the parameter is amplitude and the condition is having the greatest amplitude.

A further aspect is a method for inspecting a radius of a part having non-parallel first and second planar members connected by the radius, comprising:

(a) generating a cross-sectional model of a probe in contact with a part comprising first and second surfaces connected by a radius surface, the cross-sectional model comprising: (i) first and second lines representing respective cross sections of the first and second surfaces of the part, (ii) first through M-th curved line segments which span an expected total range of variation of a radius dimension of the radius surface of the part, each of the first through M-th curved line segments terminating at the first and second lines, wherein M is a positive integer greater than unity, and (iii) a multiplicity of points spaced at equal intervals along a curve indicative of the position of an array of transducer elements;

(b) calculating first through M-th sets of transmission focal laws for controlling the transducer elements to transmit first through M-th pluralities of beams respectively directed normal to first through M-th pluralities of target locations, wherein each of the first through M-th pluralities of target locations includes N target locations spaced along a respective one of the first through M-th curved line segments, wherein N is a positive integer greater than unity and each of the first through M-th sets of transmission focal laws comprises N transmission focal laws;

(c) calculating first through M-th sets of reception focal laws for forming first through M-th pluralities of return signals representing respective echoes returned to the transducer elements from the first through M-th pluralities of target locations, wherein each of the first through M-th sets of reception focal laws comprises N reception focal laws;

(d) placing the probe in a first position relative to the part, wherein the position of the probe relative to the part in a cross-sectional plane conforms to the relative position represented by the cross-sectional model;

(e) pulsing transducer elements of the array to respectively transmit the first through M-th pluralities of beams respectively directed normal to the first through M-th pluralities of target locations in accordance with the first through M-th sets of transmission focal laws;

(f) processing transducer output signals from the transducer elements in accordance with the first through M-th sets of reception focal laws to derive first through M-th sets of parameter values respectively characterizing the strength of the respective echoes received from the first through M-th pluralities of target locations, each of the first through M-th sets of parameter values comprising N parameter values;

(g) selecting one of the first through M-th sets of parameter values that satisfies a condition; and (h) displaying a column of N pixels having first through N-th pixel values, each of the first through N-th pixel values being a function of the respective N parameter values of the set selected in step (g).

The condition to be satisfied is that the selected set of the first through M-th sets of parameter values represents the best signal response. In one implementation, the method further comprises comparing corresponding parameter values in the first through M-th sets of parameter values to each other, wherein the best signal response is that the selected set of the first through M-th sets of parameter values includes the most parameter values which are the greatest in magnitude when compared to corresponding parameter values in the non-selected sets of the first through M-th sets of parameter values.

Yet another aspect of the subject matter disclosed herein is a method for inspecting a filleted join region of a part comprising a web and a flange connected by the filleted join region, a surface of the filleted join region having a radius dimension that varies along its length, comprising:

(a) placing an array of transducer elements so that a scan plane of the array intersects the filleted join region at a lengthwise position;

(b) pulsing the transducer elements of the array to transmit a multiplicity of beams which are respectively directed normal to a multiplicity of target locations lying in the scan plane intersecting the lengthwise position, the multiplicity of target locations comprising first through N-th pluralities of target locations arranged in a pattern comprising first through M-th curved line segments which span an expected total range of variation of a radius dimension of the filleted join region in a lengthwise direction, wherein N and M are positive integers greater than unity, each of the first through N-th pluralities of target locations consisting of first through M-th target locations respectively located along the first through M-th curved line segments of the pattern;

(c) processing transducer output signals from the transducer elements in accordance with first through M-th sets of reception focal laws to derive first through M-th sets of parameter values respectively characterizing the strength of the respective echoes received from the first through N-th pluralities of the first multiplicity of target locations;

(d) selecting one of the first through M-th sets of parameter values that satisfies a condition; and (e) displaying a first column of N pixels having first through N-th pixel values, each of the first through N-th pixel values being a function of the respective N parameter values of the set selected in step (d).

A further aspect is a system for scanning a radius of a part comprising: an array of transducer elements having a scan plane; a probe body that holds the array transducer elements; and a pulser/receiver unit programmed to perform the following operations: (a) pulsing the transducer elements of the array to transmit a multiplicity of beams which are respectively directed normal to a multiplicity of target locations lying in the scan plane, the multiplicity of target locations comprising first through N-th pluralities of target locations arranged in a pattern comprising first through M-th curved line segments which span an expected total range of variation of a radius dimension of the filleted join region in a lengthwise direction, wherein N and M are positive integers greater than unity, each of the first through N-th pluralities of target locations consisting of first through M-th target locations respectively located along the first through M-th curved line segments of the pattern; and (b) processing transducer output signals from the transducer elements to derive first through M-th sets of parameter values, each set comprising N parameter values, the M×N parameter values characterizing the strength of the respective echoes received from M×N target locations of the first through N-th pluralities of target locations.

The system described in the preceding paragraph may further comprise a display unit comprising rows and columns of pixels, and a computer system programmed to perform the following operations: (c) selecting one of the first through M-th sets of parameter values that satisfies a condition; and (d) controlling the display unit to display a column of N pixels having first through N-th pixel values, each of the first through N-th pixel values being a function of the set of parameter values selected in operation (c).

The system and methodology disclosed herein provide the ability to inspect multiple radii having different radius dimensions without having to mechanically adjust the ultrasonic probe. The disclosed system is also able to inspect many parts with different radius dimensions using one non-adjustable ultrasonic probe. The method comprises creating and displaying a C-scan pixel that is based upon the best signal response from multiple wavefronts. The system further has the ability to create and select best wavefront properties over varying radius parts so that the parts can be inspected in a rapid manner. The system disclosed herein also has the ability to inspect soft tooling radius designs that may vary in an unpredictable manner, within limits, but beyond the tolerance limits of fixed-probe ultrasonic inspection methods.

Other aspects are disclosed and claimed below.

BRIEF DESCRIPTION OF THE DRAWINGS

Reference will hereinafter be made to the drawings in which similar elements in different drawings bear the same reference numerals.

DETAILED DESCRIPTION

For ultrasonic inspection of composite structure, the ultrasound beam should ideally enter at 90 degrees to the local surface of the composite part being inspected. If it does not enter at 90 degrees, it will be refracted off normal and a return echo from any possible internal structure or anomaly will not be optimum. Traditionally a 90-degree entry angle is maintained by holding a sensor array at a precisely fixed position in space relative to the surface.

A process for non-destructive inspection of parts of variable and irregular shape will now be described. The process comprises transmitting a sequence of ultrasound beams focused at a multiplicity of target locations located at different depths within a small volume of space and then using the best (i.e., strongest) echo to calculate a pixel value for a display pixel. This process is repeated for multiple small volumes in each scan plane to calculate pixel values for each column of pixels on a display screen. Selecting the strongest echo ensures that the sound enters the inspected part at or nearly at 90 degrees or normal to the confronting portion of a radius surface.

The process described in the preceding paragraph may, for example, be applied in inspection of soft-tooled composite parts such as wing panel stringers made of fiber-reinforced plastic. The filleted join regions (i.e., radii) of such parts, whether they are designed to be constant or to vary by part location, will "vary by manufacturing". This fact creates a difficult and unique mechanical challenge to design and build an apparatus that can maintain sensor-to-part surface normality over a challenging and not-known-in-advance variety of "radial" shapes. Normality over a range of radii within a design tolerance can be maintained using the data acquisition/analysis techniques and mechanical design disclosed herein.

Figure 1:
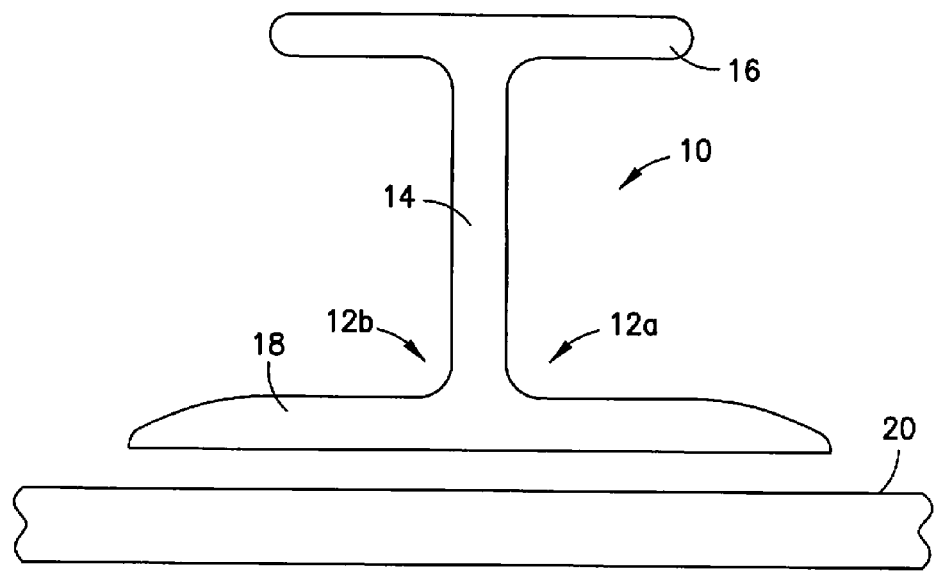
FIG. 1 is a diagram showing an exploded end view of a typical composite skin and I-shaped stringer assembly.

FIG. 1 is an exploded, partial cross-sectional view of a typical composite skin and stringer assembly. The composite skin and stringer assembly comprises an elongated stringer 10 having a web 14 that is positioned between a first flange 16 and an opposing second flange 18. The web 14 may have a height designed to provide a desired resistance to an applied loading. The first and second flange portions 16/18 may be generally planar members. The web 14 and first and second flanges 16/18 may be constant along a span of the stringer (i.e. into the page), or they may vary continuously or non-continuously along the span of the stringer 10. The web 14 and first and second flanges 16/18 are formed from fiber-reinforced plastic material having multiple plies. The assembly also includes a skin 20 to which the second flange 18 is attached, using, for example, a suitable adhesive material. The skin 20 is also made of fiber-reinforced plastic material.

Prior to attachment of the stringer 10 to the skin 20, it is customary to inspect the stringer 10 for defects. In particular, each radius 12a/12b can be subjected to non-destructive inspection using a radius scanner platform that travels along the length of the stringer 10. In accordance with the embodiments disclosed herein, the radius scanner platform carries an ultrasonic probe that transmits sequences of ultrasound beams at a multiplicity of target locations in each of a multiplicity of axially spaced planes and forms a corresponding return signal for each echo returned to the probe. The best return signals are then selected by a data processor and converted into respective pixel values, thereby ensuring that surviving information is a function of the sound entering each radius 12a/12b at or nearly at 90 degrees relative to its surface.

Figure 2:
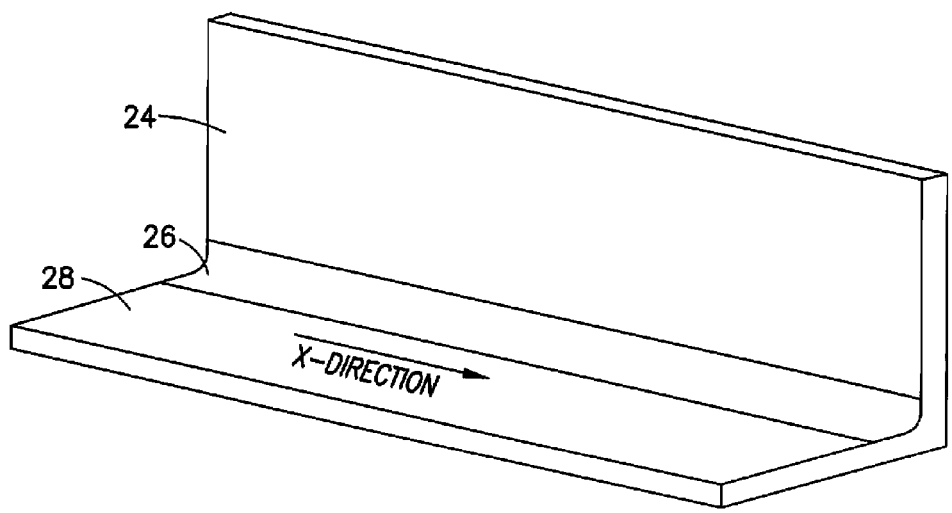
FIG. 2 is a diagram showing an isometric view of a portion of an L-shaped stringer with a circular radius. The arrow indicates a direction of travel of a scanner during inspection of the radius, which direction will be referred to herein as the X-direction.

In the example depicted in FIG. 1, the stringer 10 has an I-shaped cross-sectional profile. The NDI system disclosed herein also has application in the inspection of radii of composite parts having alternative geometries. For example, FIG. 2 shows a portion of an L-shaped composite part 22 to be inspected. The inspected part 22 comprises a web 24, a flange 28 (forming an obtuse angle with the web 24) and a radius 26. Using the inspection technique disclosed herein, the radius 26 can be scanned in a series of parallel planes normal to X and separated by equal distances. This is accomplished by moving an ultrasonic transducer array (not shown in FIG. 2) a predetermined incremental distance after each plane has been scanned. The scanner will travel along the length of the radius 26 in an X-direction (indicated by the arrow in FIG. 2).

One embodiment of a methodology for scanning a radius of unknown radius dimension will now be described. For the purpose of illustration, the inspected part is assumed to be made of composite material and comprises a flange, a web and a filleted join region, also referred to herein as a "radius" (previously defined).

Figure 3:
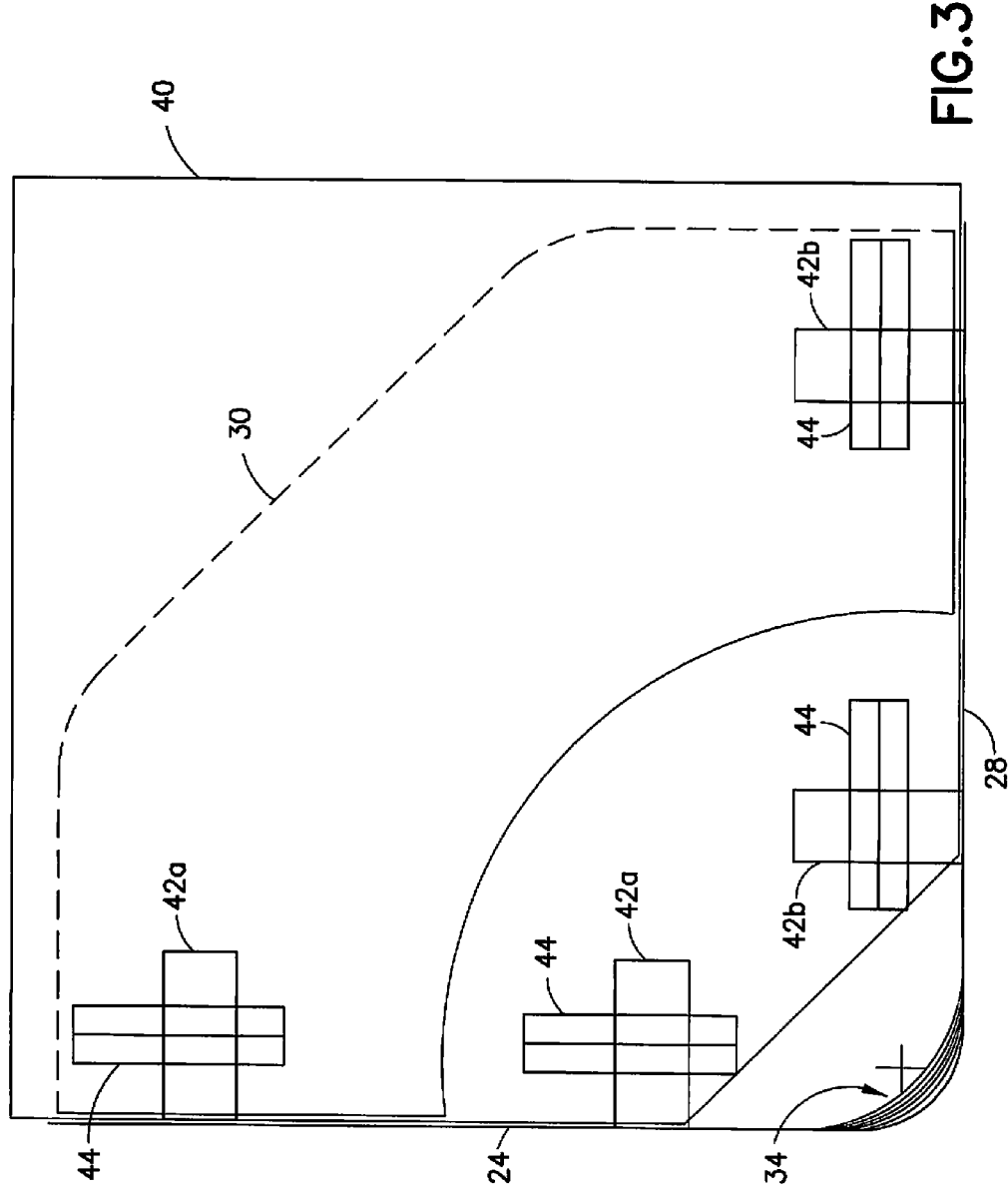
FIG. 3 is a diagram representing a CAD model of an inspection probe and a part having a radius to be inspected.

In accordance with the inspection methodology disclosed herein, the scanning system is programmed to transmit a respective multiplicity of ultrasound beams in each scan plane, each multiplicity of ultrasound beams being respectively directed normal to and optionally focused at a corresponding multiplicity of pre-calculated target locations (located relative to the coordinate system of the transducer array) in each scan plane. The scan program is determined by first generating a cross-sectional CAD model (depicted in FIG. 3) of a probe body 40 in a predetermined position relative to a part designed to comprise a web 24 and a flange 28 connected by a filleted join region (i.e., "radius"). The radius is designed to have a surface whose cross-sectional shape is a curved line segment. The CAD model further includes a curved line representing a curved ultrasonic transducer array 30 and lines representing a plurality of bearings comprising rollers 42 rotatably mounted on axles 44. The ultrasonic transducer array 30 is located in the probe body and the probe body is located relative to the part, taking into account that respective sets of rollers 42 will be in contact with web 24 and flange 28, as seen in FIG. 3. Based on known geometry and dimensions of the probe and part, the position of the transducer array 30 relative to web 24 and flange 28 is known from the CAD model. The relative positions of individual transducers are included in these values determined from the CAD model.

In other embodiments, the ultrasonic transducer array is straight and/or the probe has sliding contacts instead of bearings, which configuration will be incorporated in the CAD model.

In the cross-sectional CAD model depicted in FIG. 3, the radius of the part to be inspected is represented by a family of curved line segments 34 which span an expected total range of variation of a radius dimension of the radius surface. For the purpose of illustration, an embodiment will be described in which the curved line segments 34 are non-concentric circular line segments having different radius dimensions. The curved line segments 34 intersect the web 24 and flange 28. Ideally, the web 24 and flange 28 have planar surfaces represented by straight lines in the cross-sectional CAD model. The curved line segments 34 are drawn in the CAD model so that the straight lines representing the surfaces of web 24 and flange 28 will be tangent to each of the curved line segments 34 at respective endpoints of the latter. If the filleted radius of the part is non-circular, actual surface shapes are entered into the CAD model. In one embodiment of the method, a family of non-circular shapes is entered from physical cross-sectional microphotographs of the part to be inspected. [0]

During an inspection procedure, the probe body 40 will be placed in a position relative to the part such that its position in a cross-sectional plane conforms to the relative position represented by the cross-sectional model shown in FIG. 3.

Figure 4:
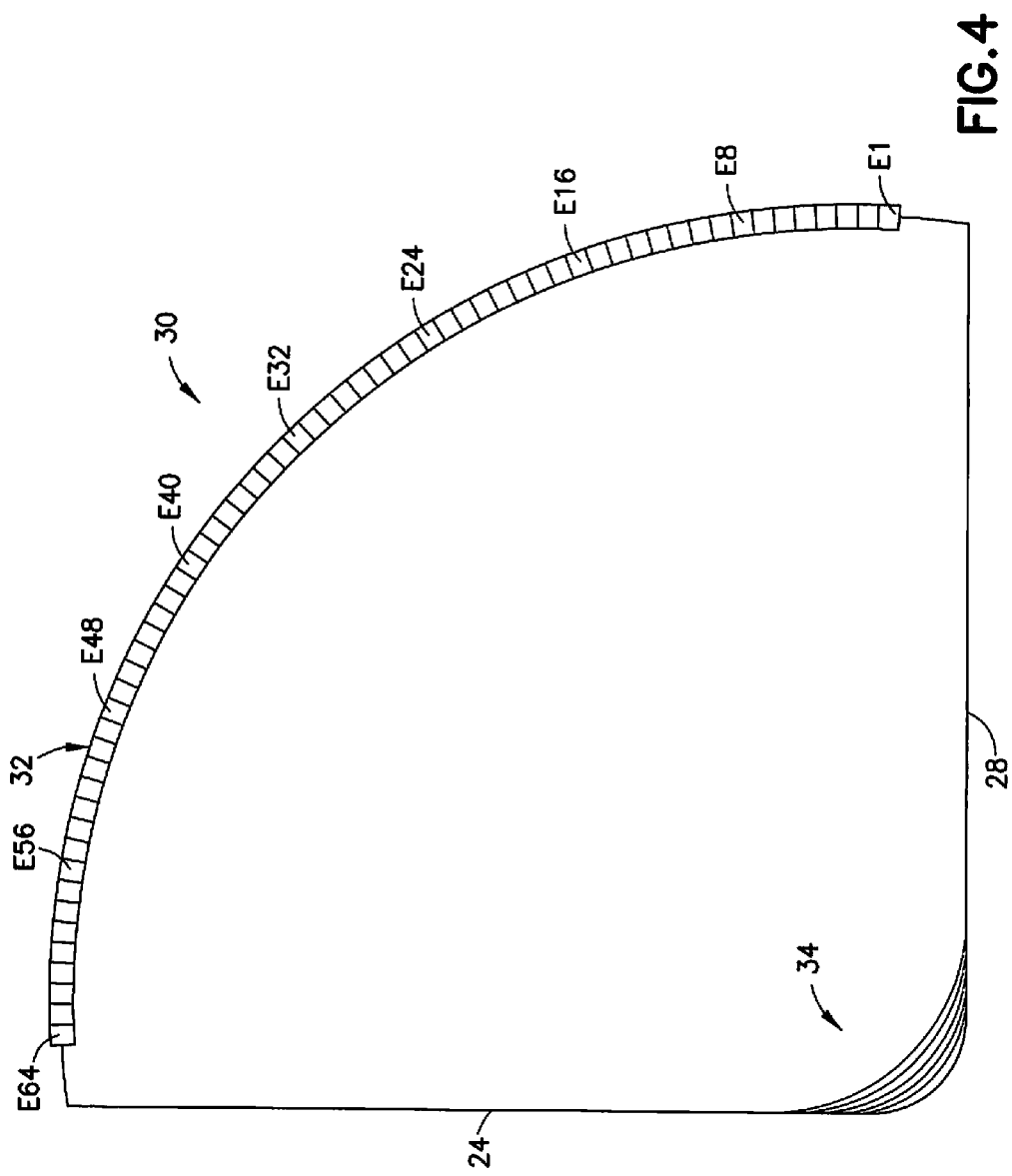
FIG. 4 is a diagram showing the position of an array of ultrasonic transducer elements relative to a family of curves (i.e., segments of circles) representing respective radius surfaces having different radius dimensions.

FIG. 4 shows the position of a curved ultrasonic transducer array 30 relative to the family of curved line segments 34 during an inspection procedure. In this implementation, the ultrasonic transducer array 30 comprises a multiplicity of transducer elements 32 arrayed side by side along a circular arc. In the implementation depicted, there are 64 transducer elements respectively numbered E1 through E64. However, it should be understood that the non-destructive inspection techniques disclosed herein do not require that the array have 64 transducer elements. The ultrasonic transducer array 30 could have more or fewer transducer elements.

To form a focused ultrasound beam, only a subset of the transducer elements E1-E64 are pulsed. For example, a group of adjacent transducer elements E31-E42 can be sequentially activated in accordance with transmission focal laws designed to produce a focused beam having a specified focal length and steering angle. The focal length and steering angle are selected such that the transmitted beam will be directed normal to a particular curve at a desired target location. Such a grouping of sequentially activated elements will be referred to herein as an "aperture". As is well known to persons skilled in the art, for each transmitted beam the same aperture will be employed to detect the echo response and convert that echo response into a respective plurality of transducer output signals. As explained in more detail below, for each set of target locations, these pluralities of echo signals are processed to determine which plurality of echo signals corresponds to the echo produced by the transmitted beam that entered the radius surface of the part at an angle most nearly normal to that radius surface at the point of impingement.

As is well understood in the art, one set of focal laws are applied when the elements of an aperture are transmitting while another set of focal laws are applied when the same elements transduce the echo response to form respective electrical output signals. The focal laws for transmitting versus receiving are different yet related by the fact that the reception focal laws are designed to detect, for each transmitted beam having a focal length and a steering angle, a respective diverging receive beam originating from a location at the same focal length and same steering angle. For example, the time delays applied to elements E31-E42 for detecting a receive beam from a target location will be the same as those for the beam transmitted by elements E31-E42 to that target location, but the sequence in which electrical echo data is acquired from elements E31-E42 will be the reverse of the sequence in which those elements were pulsed.

Still referring to FIG. 4, the separation between the curved line segments 34 should be small enough to ensure that differences in ultrasound response between target locations of adjacent curves will be acceptable. In one implementation employing six curved line segments 34 which are circular and not concentric, adjacent curved line segments 34 are separated by 0.025 inch, resulting in a family of curved line segments 34 having the following radius dimensions: 0.125, 0.150, 0.175, 0.200, 0.225, and 0.250 inch.

Figure 5:
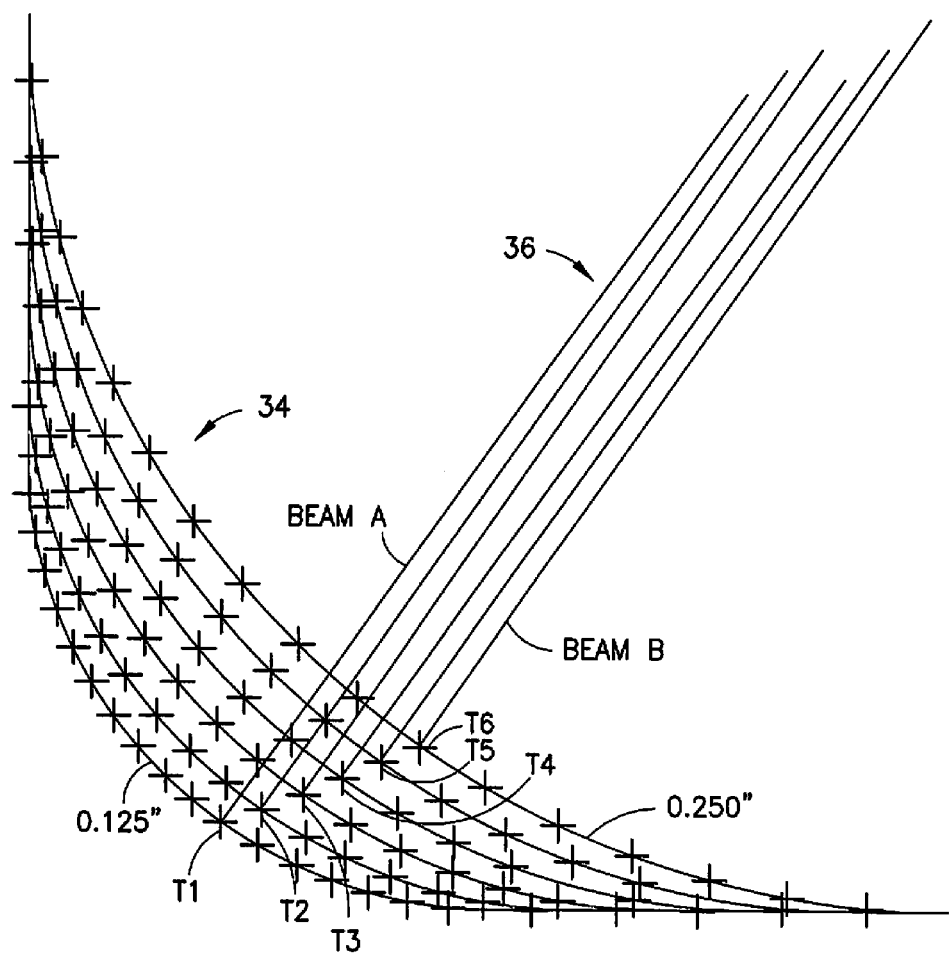
FIG. 5 is a diagram showing a group of ultrasound beams directed normal to respective points along a family of curves representing respective radii having different radius dimensions, which points correspond to a single display pixel.

FIG. 5 is a diagram showing a group of six ultrasound beams 36 focused at respective target locations T1 through T6 (each target location is indicated by a "+" symbol) along a family of six curved line segments 34 having the aforementioned respective radius dimensions 0.125, 0.150, 0.175, 0.200, 0.225, and 0.250 inch. (Although FIG. 5 shows six beams, it should be understood that these beams are transmitted at different times and are only shown together in FIG. 5 for convenience.) The six target locations T1-T6 correspond to a single display pixel (not shown), meaning that a single pixel value will be derived from the six echoes returned to the ultrasonic transducer array 30 from target locations T1-T6.

Each row of pixels on the display screen represents a specified number of degrees which differs for each of the curved line segments 34. For N rows of pixels (N is a positive integer greater than unity), each of the curved line segments 34 will have N target locations. As the radius dimension of the curved line segments 34 decreases, the same number of target locations are crowded along a shorter arc length. For example, as seen in FIG. 5, the target locations for the curved line segment of radius dimension 0.125 inch are spaced closer together than are the target locations for the curved line segment of radius dimension 0.250 inch. The target locations are spaced along each curved line segment 34 at angular increments equal to $\theta/N$, where $\theta$ is the angle subtended by the curved line segment. In the example depicted in FIG. 5, $\theta=90°$, $N=17$, and $\theta/N=5.3°$.

Still referring to FIG. 5, the structural state of the portion of the radius in the volume of space containing target locations T1-T6 will be displayed in the pixel in Row 7 of the pixel display. Each of the six ultrasound beams 36 is focused at a respective one of the target locations T1-T6. The focusing of ultrasound beams at a target location is done electronically by phasing the elements in the transducer array. The phasing is done in accordance with predetermined focal laws. Based on the previously described cross-sectional CAD model, a set of transmission focal laws are calculated for controlling the transducer elements to transmit ultrasound beams respectively focused at target locations T1-T6. In addition, a set of reception focal laws is calculated for forming a plurality of return signals representing respective echoes (i.e., receive beams) returned to the transducer array from target locations T1-T6. The same process of calculating focal laws is also performed for target locations corresponding to other pixels in a column of display pixels.

Figure 9:
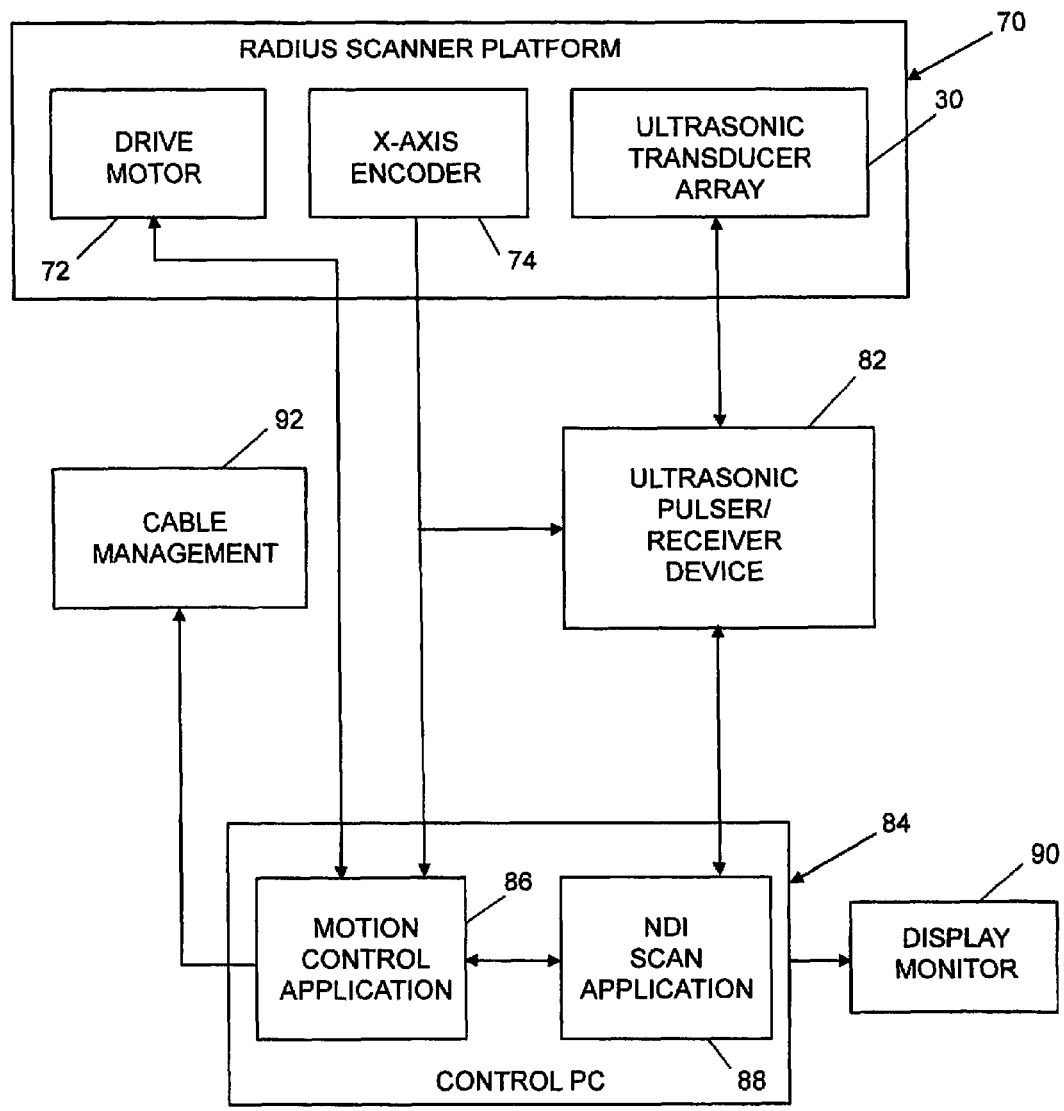
FIG. 9 is a block diagram showing a control system in accordance with one embodiment.

As seen in FIG. 9, an ultrasonic pulser/receiver device 82 is connected to the ultrasonic transducer array 30 for pulsing the transducer elements of an aperture and processing transducer output signals from the transducer elements of the same aperture in accordance with the pre-calculated focal laws. The ultrasonic pulser/receiver device 82 comprises a processor for running a software application that incorporates the respective pre-calculated focal laws for each pixel in a display column. The system depicted in FIG. 9 will be discussed in more detail later.

Returning to the implementation depicted in FIG. 5, transducer elements are pulsed to transmit (at different times) a plurality of ultrasound beams 36 focused at the respective target locations T1-T6 in accordance with a first set of focal laws. Respective echoes are returned to the same transducer elements that were pulsed from target locations T1-T6. These transducer elements convert the received ultrasonic energy into transducer output signals. These transducer output signals are time-delayed by the ultrasonic pulser/receiver device 82 (see FIG. 9) in accordance with a second set of focal laws using known gating techniques. The gated signals are then gain-corrected to compensate for different amounts of energy loss caused by transmission inefficiency at higher angles and then the gain-corrected signals are summed by the ultrasonic pulser/receiver device 82 to form a return signal representing a parameter value characterizing the strength of the echo received from that target location. The parameter values corresponding to a group of target locations are processed by a computer (see control PC 84 in FIG. 9) to determine which focused transmit beam produced the strongest echo. For example, if the true radius dimension of the part radius is 0.125 inch, then the beam impinging on target location T1 (i.e., Beam A) should produce the strongest echo. Alternatively, if the true radius dimension of the part radius is 0.250 inch, then the beam impinging on target location T6 (i.e., Beam B) should produce the strongest echo.

Figure 6:
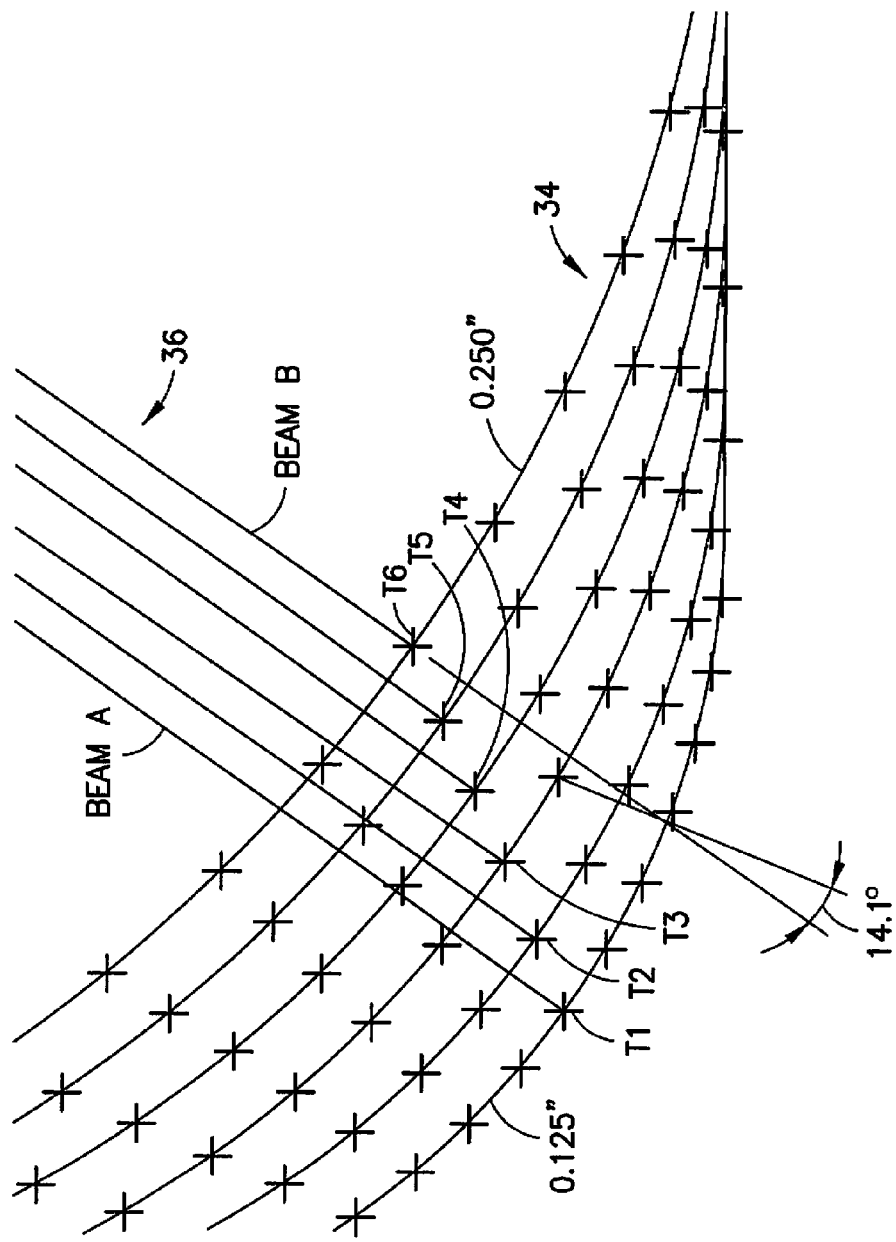
FIG. 6 is a diagram showing a portion of FIG. 5 on a magnified scale.

FIG. 6 shows a portion of FIG. 5 on a magnified scale. The strongest front surface echo produced by a beam focused at one of target locations T1-T6 will be effectively chosen by selecting the return signal corresponding to such echo. That return signal is most likely to contain information concerning the structural state of the radius in the volume element to be displayed in the Row 7 pixel. For example, the echo produced by Beam B will not be chosen for display in the Row 7 pixel if the radius surface has a radius dimension of 0.125 inch because Beam B is off normal by about 14 degrees. For the same reason, Beam A will not be chosen for display in the Row 7 pixel if the radius surface has a radius dimension of 0.250 inch.

Knowing the radius dimension at the location of a defect, well-known area correction factors can be used for sizing the defect. An area correction factor can be calculated using the following equation:

$$\text{Correction Factor} = R_f/R_a$$

where $R_f$ is the distance from the defect to the radius center of curvature, and $R_a$ is the radius of the array. The distance $R_f = r + d$, where r is the local radius dimension and d is the depth of the flaw.

In accordance with one embodiment, a computer system can be programmed to process the transducer output signals produced in response to echoes from a plurality of target locations corresponding to a single display pixel to derive a set of parameter values which respectively characterize the strengths of those echoes. One parameter value in that set which satisfies a condition (e.g., greatest amplitude) is then selected and used to calculate the pixel value for display in that pixel. The resulting pixel value will be a function of the amplitude of the strongest echo. (Alternatively, a pixel value that is a function of a weighted sum or an interpolation of two parameter values meeting certain criteria could be displayed.) The foregoing process can be repeated for each pixel in a column of pixels while the probe is stationary at a lengthwise position relative to the part being inspected.

In accordance with another implementation, one of first through M-th sets of parameter values that satisfies a condition is selected, each of said first through M-th sets of parameter values being acquired from respective first through M-th pluralities of target locations arranged along respective first through M-th curved line segments in space, each plurality of target locations including N target locations, where M and N are positive integers greater than unity. This method further comprises displaying a column of N pixels having first through N-th pixel values, each of the first through N-th pixel values being a function of the respective N parameter values of the set of first through M-th parameter values which was selected. The condition to be satisfied is that the selected set of the first through M-th sets of parameter values represents the best signal response.

In accordance with one implementation, the method further comprises comparing corresponding parameter values in the first through M-th sets of parameter values to each other, wherein the best signal response is that the selected set of the first through M-th sets of parameter values includes the most parameter values which are the greatest in magnitude when compared to corresponding parameter values in the non-selected sets of the first through M-th sets of parameter values. For example, a majority rule may be employed which works as follows: If there are three sets of line segments and each curved line segment has 25 target locations, this results in 75 beams and 75 front surface echoes. If, e.g., nine (or some other number) maximum front surface echoes come from the target locations along a single curved line segment, the response from those target locations is used to populate the column of display pixels. In this example, a column of pixels for final display will not be a combination of return signals coming from different beam sets, it will be a display of one beam set based on the majority rule.

Multiple columns of pixels will be displayed, each column of pixels corresponding to a respective lengthwise position of the probe. In one implementation, the probe is carried on a platform that is moved in a lengthwise direction intermittently in equal increments.

Figure 7:
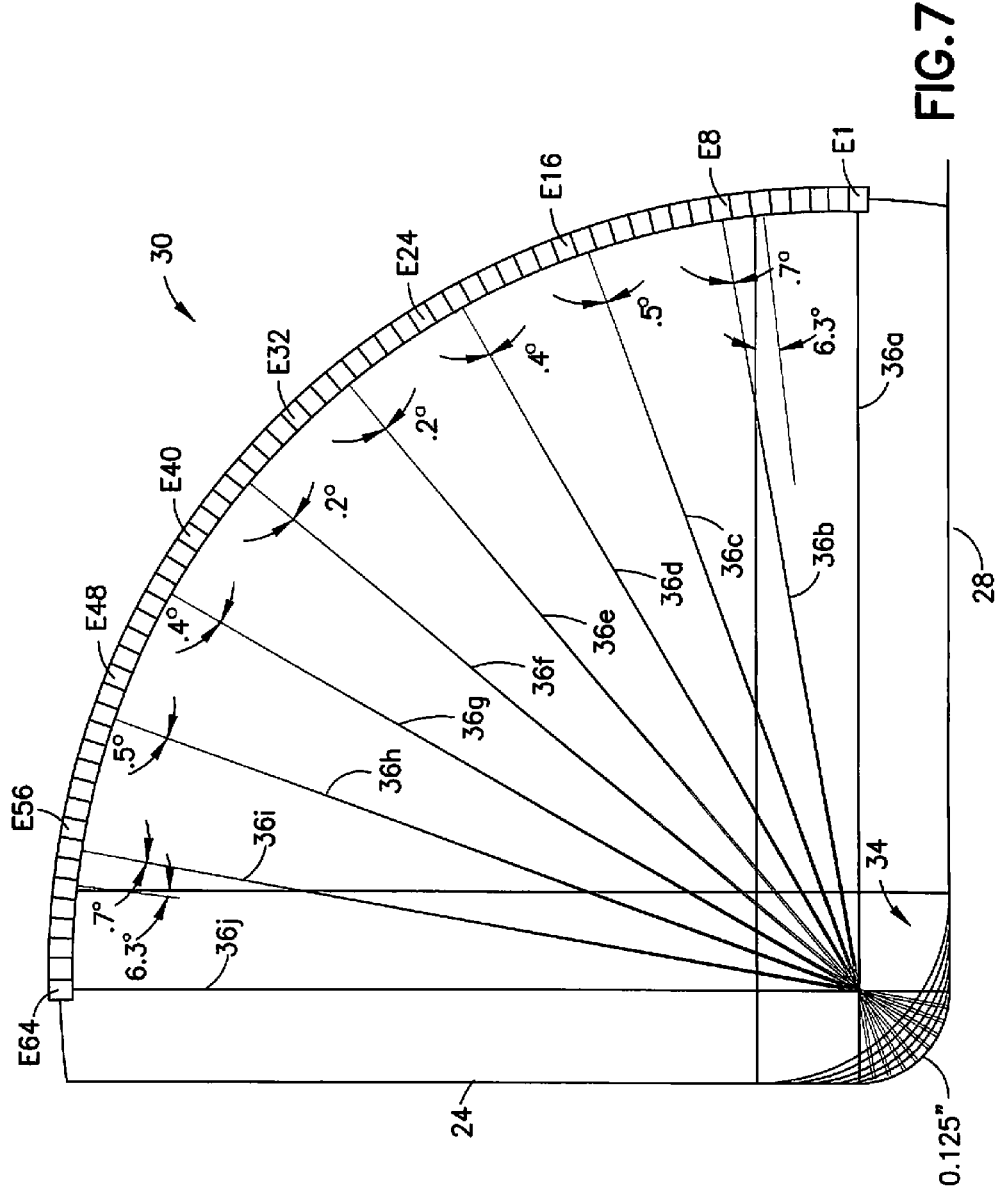
FIG. 7 is a diagram showing a group of ultrasound beams focused at respective points along a single curve corresponding to a single column of display pixels.

FIG. 7 shows eight ultrasound beams 36a through 36j directed toward corresponding target locations on the curved line segment having a radius dimension of 0.125 inch. Similar diagrams could be drawn to show beams focused on target locations on the other curved line segments having respective radius dimensions of 0.150, 0.175, 0.200, 0.225, and 0.250 inch. The transducer apertures for any plurality of six target locations corresponding to a single display pixel may be different for different curved line segments. Also, the same transducer aperture can be employed for two or more of the six target locations. For example, in the case of target locations T1-T6 seen in FIG. 6, a first transducer aperture could be utilized to transmit beams focused at target locations T1 and T2; a second transducer aperture (different than the first transducer aperture) could be utilized to transmit beams focused at target locations T3 and T4; and a third transducer aperture (different than the first and second transducer apertures) could be utilized to transmit beams focused at target locations T5 and T6. Moreover, such different transducer apertures could be overlapping. For example, the first transducer aperture could consist of transducer elements E31-E42, the second transducer aperture could consist of transducer elements E35-E46, and so forth. In addition, the number of transducer elements included in an aperture can vary depending on the location of the aperture along the curved transducer array.

Figure 8:
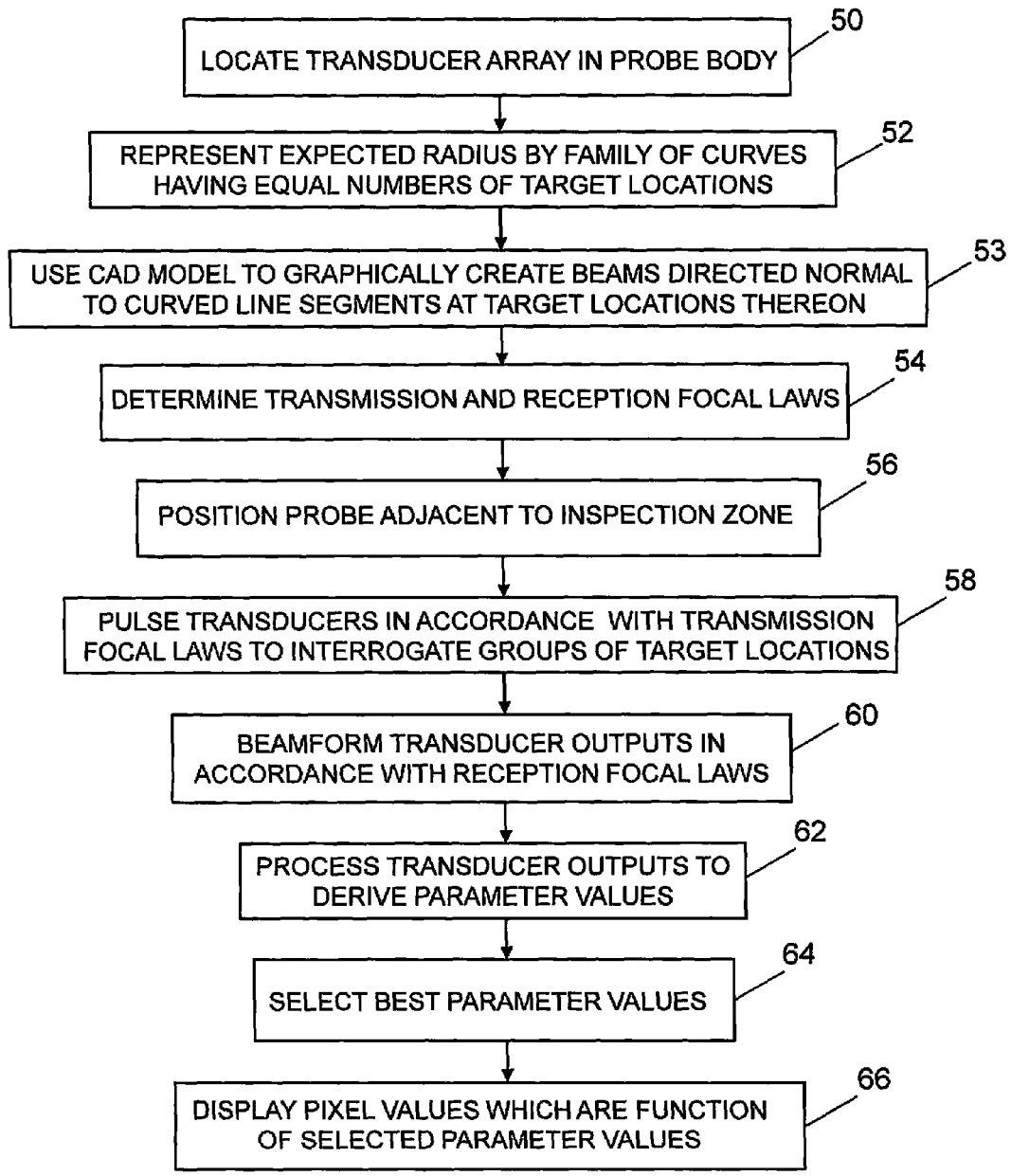
FIG. 8 is a flowchart showing steps of a method for ultrasonic data acquisition in accordance with one embodiment.

FIG. 8 is a flowchart showing steps of a process for designing and implementing a system for inspecting a radius of a part having an unknown radius dimension. The first stage in the process is to locate a curved transducer array in a probe body (step 50). Then a cross-sectional CAD model of the probe in contact with the part to be inspected is generated. The part may comprise non-parallel first and second surfaces (e.g., planar surfaces) connected by a radiused surface. The cross-sectional model comprises first and second lines representing respective cross sections of the first and second surfaces. Because the true radius dimension of the radiused surface of the part to be inspected is not known, the expected radius is represented in the CAD model by a plurality of curved line segments having different radius dimensions which span an expected total range of variation of the radius dimension (step 52). Each of the curved line segments terminates at the first and second lines.

Using the CAD model, ultrasonic beams directed normal to the curved line segments at targeted locations on those line segments are graphically created (step 53). Using the defined beams, sets of transmission and reception focal laws are calculated (step 54). More precisely, a set of transmission focal laws are calculated for controlling the transducer elements to emit a multiplicity beams respectively focused at a multiplicity of target locations respectively located on the plurality of curved line segments. In addition, a set of reception focal laws are calculated which are designed to receive respective return signals representing respective echoes returned to the transducer elements from the multiplicity of target locations. These focal laws are then programmed into a pulser/receiver device to which the probe is connected.

Then probe is then positioned adjacent to the inspection zone (step 56). More specifically, the probe is placed in a position relative to the part which conforms to the relative position represented by the cross-sectional CAD model. The scan plane of the ultrasonic transducer array is preferably perpendicular to the longitudinal axis of the part to be inspected. The probe can be moved intermittently in increments in a lengthwise direction starting at an initial position and stopping at a final position.

Still referring to FIG. 8, nondestructive inspection is carried out by pulsing one or more groups of transducer elements of the array to transmit a plurality of beams toward the plurality of target locations in accordance with the transmission focal laws (step 58). As previously mentioned, different (possibly overlapping) apertures can be used to interrogate respective target locations of the plurality of target locations corresponding to a single display pixel. After each beam is emitted, the resulting echoes include ultrasound waves that impinge on the same transducer elements included in the transmission aperture for each beam. Those transducer elements will transmit the impinging ultrasound waves into electrical transducer output signals. Those transducer output signals are time delayed in accordance with the reception focal laws (step 60). Optionally, the time-delayed transducer output signals are gain corrected. The transducer output signals are then summed to form signals representing first through M-th sets of parameter values corresponding to the amplitudes of the respective receive beams from the target locations arranged along first through M-th (e.g., M=6 in FIG. 6) curved line segments (step 62). The best parameter values are then selected (step 64) and then converted into respective pixel values for display (step 66). In the example shown in FIG. 6, each of the first through M-th sets of parameter values comprises N=17 parameter values corresponding to the N=17 target locations arranged along each curved line segment. Depending on which algorithm is used, the "best" parameter values may comprise the parameter values corresponding to target locations along a single curved line segment or target locations along different curved line segments.

In accordance with one embodiment, the ultrasound beams are fired consecutively after a set distance of probe movement along the length of the composite part (e.g., in the X-direction seen in FIG. 2). The set distance of probe movement serves as the scan resolution and this distance is obtained from an encoder attached to the mobile platform that carries the probe. In accordance with one implementation, each scan plane is perpendicular to the X-axis and separated from adjacent scan planes by the aforementioned set distance. This spacing determines the horizontal resolution of the pixel image to be displayed. Preferably the resolution is the same in the vertical direction, meaning that the targets will be located along an arc length defined by the intersection of the scan plane and the radius. These targets will preferably be spaced apart by the aforementioned set distance.

An apparatus for inspecting filleted join regions (i.e., "radii") of an elongated composite part will now be described with reference to FIG. 9. The apparatus comprises a mobile radius scanner platform 70 that carries at least one ultrasonic transducer array 30. In accordance with one embodiment, the control system comprises a ground-based computer 84 programmed with motion control application software 86 and NDI scan application software 88. The control computer 84 is connected to an electronics box (not shown). The electronics box in turn is connected to the radius scanner platform 70 via a flexible electrical cable (not shown). The electronics box contains the system power supplies and integrates all the scanner control connections and provides an interface between the computer and radius scanner platform 70.

In accordance with one implementation, the computer 84 may comprise a general-purpose computer programmed with a motion control application 86 comprising a software module for controlling a drive motor 72 which causes the radius scanner platform 70 to move in the X-direction. The motion control application 86 also controls a motor (not shown) of a cable management system 92. The cable management system 92 consists of two sets of motorized wheels (not shown) that respectively grip the cables connecting the operations control center to the radius scanner platform 70. The motor of the cable management system 92 is under computer control, which synchronizes the cables with the movement of the radius scanner platform 70, extending or retracting the cables as appropriate.

In the alternative, the methodology disclosed and claimed herein can be employed using manual probes that have no motors.

In accordance with one embodiment, an X-axis displacement encoder 74 is mounted to the radius scanner platform 70 (e.g., a rotational encoder attached to an idler wheel). Encoded X-axis position data from X-axis displacement encoder 74 (in the form of encoder pulses) is received by the ultrasonic pulser/receiver device 82, which in turn sends those encoder pulses to the NDI scan application 88. The NDI scan application 88 uses these pulses to position the scan data in the proper location on a display monitor 90.

The X-motion drive motor 72 can be a programmable stepper motor that can communicate with the computer 84 through a serial communications interface (not shown). The operator or automated path planning system specifies the desired incremental movements and an optional final goal position of the radius scanner platform 70 through the motion control application 86. The X-axis positioning is controlled using proportional feedback of the encoder count data.

The NDI scan application 88 includes ultrasonic data acquisition and display software that controls the ultrasonic pulser/receiver device 82. The ultrasonic pulser/receiver device 82 in turn sends pulses to and receives output signals from the ultrasonic transducer array 30. The NDI scan application software 88 controls all details of the scan data and the display of data. The pulser/receiver device 82 correlates the acquired ultrasonic scan data with the X-position information.

One embodiment of the control system depicted in FIG. 9 has the ability to provide meaningful distance information in a final C-scan. The C-scan presentation provides a plan-type view of the location and size of part features. The plane of the image is parallel to the scan pattern of the ultrasonic transducer array 30. In a C-scan, there is distance information shown in the display. The distance information is found along the horizontal and vertical axes (or rulers) of the display monitor 90. Individual pixels make up the C-scan. The width of each pixel directly corresponds to the resolution of the X-axis displacement encoder 74 that encodes displacement along the longitudinal axis of the part being inspected. However, the distance in the vertical direction must correlate to the distance between the beams directed at different target locations on the radius surface in a scan plane. The distance between those beams corresponds to the physical distance between the target locations. Operators can make size measurements of flaws that might show up in the C-scan. The focal laws corresponding to the selected receive beams of greatest amplitude enable calculation of the distance between the theoretical targets, which directly correlates to the height of the C-scan pixels. Optionally, this beam selection can be done during post-processing after the part has been scanned. The NDI scan application 88 includes data analysis software which is used to determine the best return signals according to the methods previously described.

Ultrasonic inspection at the frequency used by the system disclosed herein requires the presence of an acoustic couplant between the ultrasonic transducer array and the inspected part. The scanning system shown in FIG. 9 uses water as the acoustic couplant. In accordance with one embodiment, the probe body has a water cavity (not shown) which is supplied with water via a water supply tube (not shown), which is also managed by the cable management system 92. The fluid acoustic couplant is supplied into a space between the curved array of transducer elements and the radius of the part. Processing of the return signals may comprise applying respective gains to the respective return signals, the gains being selected to compensate for different amounts of energy loss caused by transmission inefficiency at higher angles. These respective gains being a function of distance of travel of each echo through the fluid acoustic couplant. Another variable is response variation between different elements of the array. Another variable is the number of elements used for each beam. Due to physical limits, the method may use six transducer elements per beam at the outer edge of the array as opposed to twelve elements per beam at the center of the array.

The X-position of the ultrasonic transducer array 30 is measured by the X-axis displacement encoder 74, which encodes rotation of an encoder wheel (not shown) mounted to the carriage frame of the radius scanner platform 70. The encoder wheel rides on a surface of the part as the radius scanner platform 70 travels along a radius. The X-axis displacement encoder 74 sends an encoder pulse to the control computer 84 after each incremental movement of the radius scanner platform 70 in the X-direction, which encoder pulses are used by control computer 84 and by ultrasonic puller/receiver device 82 to determine the X-coordinate of each scan plane in a well-known manner.

For one specific application involving the inspection of a soft-tooled radius of an integrally stiffened wing box, the above-described ultrasonic data acquisition/analysis system can be integrated into a non-destructive inspection system comprising: an active trailer vehicle that carries the ultrasonic transducer array(s) for inspecting the soft-tooled radius; an external motorized tractor used to move the active trailer vehicle through the tunnels of the wing box; one or more ultrasonic pulser/receivers connected to the ultrasonic transducer arrays; a computer that hosts the ultrasonic analysis, data acquisition and movement control software; and a monitor for displaying C-scan images of the inspected part.

Figure 10:
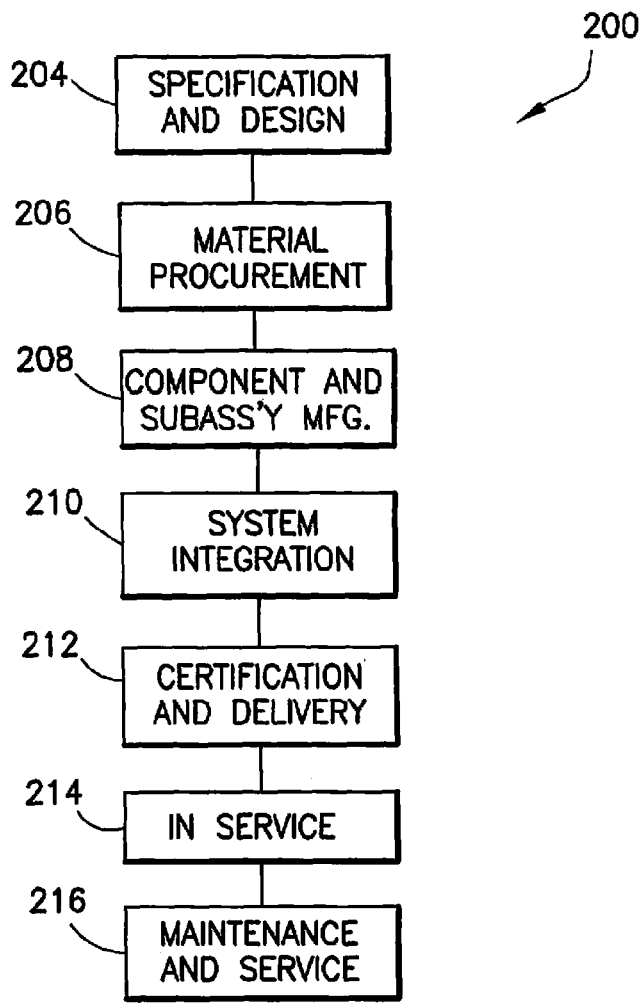
FIG. 10 is a flow diagram of an aircraft production and service methodology.
Figure 11:
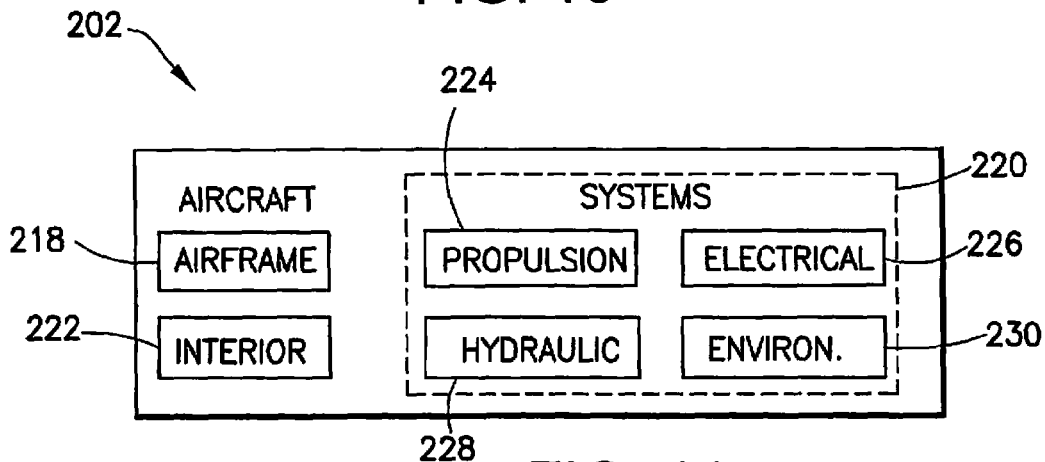
FIG. 11 is a block diagram showing systems of an aircraft.

The systems and methods disclosed above may be employed in an aircraft manufacturing and service method 200 as shown in FIG. 10 for inspecting parts of an aircraft 202 as shown in FIG. 11. During pre-production, exemplary method 200 may include specification and design 204 of the aircraft 202 and material procurement 206. During production, component and subassembly manufacturing 208 and system integration 210 of the aircraft 202 takes place. Thereafter, the aircraft 202 may go through certification and delivery 212 in order to be placed in service 214. While in service by a customer, the aircraft 202 is scheduled for routine maintenance and service 216 (which may also include modification, reconfiguration, refurbishment, and so on).

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 11, the aircraft 202 produced by exemplary method 200 may include an airframe 218 (comprising, e.g., a fuselage, frames, stiffeners, wing boxes, etc.) with a plurality of systems 220 and an interior 222. Examples of high-level systems 220 include one or more of the following: a propulsion system 224, an electrical system 226, a hydraulic system 228, and an environmental control system 230. Any number of other systems may be included. Although an aerospace example is shown, the principles disclosed herein may be applied to other industries, such as the automotive industry.

Apparatus and methods embodied herein may be employed during any one or more of the stages of the production and service method 200. For example, components or subassemblies fabricated or assembled during production process 208 may be inspected using the inspection system disclosed herein. Also, one or more apparatus embodiments, method embodiments, or a combination thereof may be utilized during the production stages 208 and 210, for example, by substantially expediting assembly of or reducing the cost of an aircraft 202. Similarly, one or more of apparatus embodiments, method embodiments, or a combination thereof may be utilized while the aircraft 202 is in service, for example and without limitation, during maintenance and service 216.

The teaching disclosed above could ultimately replace many unique NDI probe designs with a single probe design. It could allow operators to scan the radius of a wing panel or fuselage stiffener without having to mechanically adjust the probe. As an example of cost savings, an inspection technique requiring three scan passes to inspect the radii of wing panel stringers could conceivably be replaced by a single-pass radius inspection method. Due to the large numbers of composite stiffeners incorporated in some modern airplanes, the methodology disclosed herein could reduce inspection costs dramatically.

While inspection systems and methods have been described with reference to various embodiments, it will be understood by those skilled in the art that various changes may be made and equivalents may be substituted for elements thereof without departing from the scope of the invention. In addition, many modifications may be made to adapt the teachings herein to a particular situation without departing from the scope thereof. Therefore it is intended that the claims not be limited to the particular embodiments disclosed.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

Memory, which generally includes different modalities, may be implemented using random access memory, hard disk storage and/or other removable media devices, such as CD-ROM drives, which are capable of reading information stored on a computer-readable medium such as a CD-ROM.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude any portions of two or more steps being performed concurrently or alternatingly.

As used in the claims, the limitation "comparing corresponding parameter values in the first through M-th sets of parameter values to each other" means that the first parameter values of each set are compared to each other, the second parameter values of each set are compared to each other, etc.

The invention claimed is:

1. A system for scanning a radius of a part comprising:
   an array of transducer elements;
   a probe body that holds said array transducer elements; and
   a pulser/receiver unit programmed to perform the following operations:
   (a) pulsing transducer elements of the array in accordance with a first set of focal laws to emit a first plurality of beams in sequence, said beams of said first plurality of beams being respectively focused at respective target locations of a first plurality of target locations located in space along respective model curved line segments, said beams of said first plurality of beams being respectively normal to said respective model curved line segments at said respective target locations of said first plurality of target locations;
   (b) after each beam of said first plurality of beams is emitted, processing transducer output signals from the transducer elements in accordance with a second set of focal laws to derive a first set of parameter values characterizing the strengths of the respective echoes received from the first plurality of target locations;
   (c) pulsing transducer elements of the array in accordance with a third set of focal laws to emit a second plurality of beams in sequence, said beams of said second plurality of beams being respectively focused at respective target locations of a second plurality of target locations located in space along said respective model curved line segments, said beams of said second plurality of beams being respectively normal to said respective model curved line segments at said respective target locations of said second plurality of target locations; and
   (d) after each beam of said second plurality of beams is emitted, processing transducer output signals from the transducer elements in accordance with a fourth set of focal laws to derive a second set of parameter values characterizing the strengths of the respective echoes received from the second plurality of target locations,
   wherein said model curved line segments span an expected total range of variation of a radius surface of a part to be inspected.

2. The system as recited in claim 1, further comprising a computer system programmed to perform the following operations:
   (e) selecting one of said first set of parameter values that satisfies a condition; and
   (f) selecting one of said second set of parameter values that satisfies said condition.

3. The system as recited in claim 2, wherein said parameter is amplitude and said condition is having the greatest amplitude.

4. The system as recited in claim 2, further comprising a display unit comprising rows and columns of pixels, wherein said computer system is further programmed to perform the following operations:
   (g) controlling said display unit to display in a first pixel a first pixel value which is a function of at least the parameter value selected in operation (e); and
   (h) controlling said display unit to display in a second pixel a second pixel value which is a function of at least the parameter value selected in operation (f),
   wherein said first and second pixels are adjacent to each other and in the same column.

5. The system as recited in claim 1, wherein said curved line segments are non-concentric circular line segments having different radius dimensions.

6. A method for inspecting a radius of a part, comprising:
   (a) generating a cross-sectional model of a probe in contact with a part comprising first and second surfaces connected by a radius surface, the probe comprising an array of transducer elements, said cross-sectional model comprising first and second lines representing respective cross sections of said first and second surfaces and a plurality of curved line segments which span an expected total range of variation of a radius dimension of the radius surface of the part, each of said curved line segments terminating at said first and second lines;
   (b) calculating a first set of focal laws for controlling the transducer elements to emit a plurality of beams respectively directed normal to a first plurality of target locations respectively located on said curved line segments;
   (c) calculating a second set of focal laws which are designed to receive respective return signals representing respective echoes returned to the transducer elements from the first plurality of target locations;
   (d) placing the probe in a first lengthwise position relative to the part, wherein the position of the probe relative to the part in a cross-sectional plane conforms to the relative position represented by said cross-sectional model;
   (e) pulsing the transducer elements of the array to transmit a first plurality of beams respectively directed normal to the first plurality of target locations in accordance with the first set of focal laws;
   (f) after each beam of said first plurality of beams is emitted, processing transducer output signals from the transducer elements in accordance with the second set of focal laws to derive a first set of parameter values characterizing the strength of the respective echoes received from the first plurality of target locations;
   (g) selecting one of said first set of parameter values that satisfies a condition; and
   (h) displaying a first pixel value which is a function of at least the parameter value selected in step (g).

7. The method as recited in claim 6, wherein said parameter is amplitude and said condition is having the greatest amplitude.

8. The method as recited in claim 6, further comprising the following steps while the array is in the first lengthwise position:

(i) calculating a third set of focal laws for controlling the transducer elements to emit a plurality of beams respectively focused at a second plurality of target locations respectively located on said curved line segments;

(j) calculating a fourth set of focal laws which are designed to receive respective return signals representing respective echoes returned to the transducer elements from the second plurality of target locations;

(k) pulsing the transducer elements of the array to transmit a second plurality of beams toward the second plurality of target locations in accordance with the third set of focal laws;

(l) after each beam of said second plurality of beams is emitted, processing transducer output signals from the transducer elements in accordance with the fourth set of focal laws to derive a second set of parameter values characterizing the strength of the respective echoes received from the second plurality of target locations;

(m) selecting one of said second set of parameter values that satisfies said condition; and (n) displaying a second pixel value which is a function of at least the parameter value selected in step (m), wherein said second pixel value is displayed adjacent to said first pixel value.

9. The method as recited in claim 8, further comprising:
moving the probe to a second position relative to the part, said second position being displaced from said first position; and
repeating steps (e) through (h) and (l) through (n) while the probe is in the second position,
wherein the first and second pixel values corresponding to said first position are respectively displayed adjacent to the first and second pixel values corresponding to said second position.

10. A method for inspecting a radius of a part having non-parallel first and second planar members connected by the radius, comprising:
(a) generating a cross-sectional model of a probe in contact with a part comprising first and second surfaces connected by a radius surface, said cross-sectional model comprising:
(i) first and second lines representing respective cross sections of said first and second surfaces of the part,
(ii) first through M-th curved line segments which span an expected total range of variation of a radius dimension of the radius surface of the part, each of said first through M-th curved line segments terminating at said first and second lines, wherein M is a positive integer greater than unity, and
(iii) a multiplicity of points spaced at equal intervals along a curve indicative of the position of an array of transducer elements;
(b) calculating first through M-th sets of transmission focal laws for controlling the transducer elements to transmit first through M-th pluralities of beams respectively directed normal to first through M-th pluralities of target locations, wherein each of said first through M-th pluralities of target locations includes N target locations spaced along a respective one of said first through M-th curved line segments, wherein N is a positive integer greater than unity and each of said first through M-th sets of transmission focal laws comprises N transmission focal laws;
(c) calculating first through M-th sets of reception focal laws for forming first through M-th pluralities of return signals representing respective echoes returned to the transducer elements from said first through M-th pluralities of target locations, wherein each of said first through M-th sets of reception focal laws comprises N reception focal laws;

(d) placing the probe in a first position relative to the part, wherein the position of the probe relative to the part in a cross-sectional plane conforms to the relative position represented by said cross-sectional model;

(e) pulsing transducer elements of the array to respectively transmit said first through M-th pluralities of beams respectively directed normal to said first through M-th pluralities of target locations in accordance with said first through M-th sets of transmission focal laws;

(f) processing transducer output signals from the transducer elements in accordance with said first through M-th sets of reception focal laws to derive first through M-th sets of parameter values respectively characterizing the strength of the respective echoes received from said first through M-th pluralities of target locations, each of said first through M-th sets of parameter values comprising N parameter values;

(g) selecting one of said first through M-th sets of parameter values that satisfies a condition; and (h) displaying a column of N pixels having first through N-th pixel values, each of said first through N-th pixel values being a function of the respective N parameter values of the set selected in step (g).

11. The method as recited in claim 10, wherein said condition is that the selected set of said first through M-th sets of parameter values represents a best signal response from amongst signal responses for said first through M-th pluralities of target locations.

12. The method as recited in claim 11, further comprising comparing corresponding parameter values in the first through M-th sets of parameter values to each other, wherein said best signal response is that said selected set of said first through M-th sets of parameter values includes the most parameter values which are the greatest in magnitude when compared to corresponding parameter values in the non-selected sets of said first through M-th sets of parameter values.

13. The method as recited in claim 10, further comprising:
moving the probe to a second position relative to the part, said second position being displaced from said first position; and
repeating steps (e) through (h) while the probe is in the second position,
wherein the first through N-th sets of pixel values corresponding to said first position are respectively displayed adjacent to the first through N-th sets of pixel values corresponding to said second position.

14. The method as recited in claim 10, wherein said plurality of curved line segments having different radius dimensions comprise first, second and third curved line segments having first, second and third radius dimensions respectively, the difference between said first and second radius dimensions being equal to the difference between said second and third radius dimensions.

15. A method for inspecting a filleted join region of a part comprising a web and a flange connected by the filleted join region, a surface of the filleted join region having a radius dimension that varies along its length, comprising:
(a) placing an array of transducer elements so that a scan plane of the array intersects the filleted join region at a first lengthwise position;
(b) pulsing the transducer elements of the array to transmit a first multiplicity of beams which are respectively directed normal to a first multiplicity of target locations lying in the scan plane intersecting said first lengthwise position, said first multiplicity of target locations comprising first through N-th pluralities of target locations arranged in a pattern comprising first through M-th curved line segments which span an expected total range of variation of a radius dimension of the filleted join region in a lengthwise direction, wherein N and M are positive integers greater than unity, each of said first through N-th pluralities of target locations consisting of first through M-th target locations respectively located along said first through M-th curved line segments of said pattern;

(c) processing transducer output signals from the transducer elements in accordance with first through M-th sets of reception focal laws to derive first through M-th sets of parameter values respectively characterizing the strength of the respective echoes received from said first through N-th pluralities of said first multiplicity of target locations;

(d) selecting one of said first through M-th sets of parameter values that satisfies a condition; and (e) displaying a first column of N pixels having first through N-th pixel values, each of said first through N-th pixel values being a function of the respective N parameter values of the set selected in step (d).

16. The method as recited in claim 15, wherein said condition is that the selected set of said first through M-th sets of parameter values represents a best signal response from amongst signal responses for said first through M-th pluralities of target locations.

17. The method as recited in claim 16, further comprising comparing corresponding parameter values in the first through M-th sets of parameter values to each other, wherein said best signal response is that said selected set of said first through M-th sets of parameter values includes the most parameter values which are the greatest in magnitude when compared to corresponding parameter values in the non-selected sets of said first through M-th sets of parameter values.

18. The method as recited in claim 15, further comprising:

(f) moving the array of transducer elements so that a scan plane of the array intersects the filleted join region at a second lengthwise position displaced relative to said first lengthwise position;

(g) pulsing the transducer elements of the array to transmit a second multiplicity of beams which are respectively directed normal to a second multiplicity of target locations lying in the scan plane intersecting said second lengthwise position, said second multiplicity of target locations comprising first through N-th pluralities of target locations arranged in said pattern, each of said first through N-th pluralities of target locations of said second multiplicity of target locations consisting of first through M-th target locations respectively located along said first through M-th curved line segments of said pattern;

(h) processing transducer output signals from the transducer elements in accordance with said first through M-th sets of reception focal laws to derive (M+1)-th through 2M-th sets of parameter values respectively characterizing the strength of the respective echoes received from said first through N-th pluralities of said second multiplicity of target locations;

(i) selecting one of said (M+1)-th through 2M-th sets of parameter values that satisfies said condition; and (j) displaying a second column of N pixels having (N+1)-th through 2N-th pixel values, each of said (N+1)-th through 2N-th pixel values being a function of the N parameter values of the set selected in step (i), wherein said first column of N pixels is adjacent to said second column of N pixels.

19. A system for scanning a radius of a part comprising:
an array of transducer elements having a scan plane;
a probe body that holds said array of transducer elements; and
a pulser/receiver unit programmed to perform the following operations:

(a) pulsing the transducer elements of the array to transmit a multiplicity of beams which are respectively directed normal to a multiplicity of target locations lying in the scan plane, the multiplicity of target locations comprising first through N-th pluralities of target locations arranged in a pattern comprising first through M-th curved line segments which span an expected total range of variation of a radius dimension of the filleted join region in a lengthwise direction, wherein N and M are positive integers greater than unity, each of said first through N-th pluralities of target locations consisting of first through M-th target locations respectively located along said first through M-th curved line segments of said pattern; and (b) processing transducer output signals from the transducer elements to derive first through M-th sets of parameter values, each set comprising N parameter values, said M×N parameter values characterizing the strength of the respective echoes received from M×N target locations of said first through N-th pluralities of target locations.

20. The system as recited in claim 19, further comprising a display unit comprising rows and columns of pixels, and a computer system programmed to perform the following operations:

(c) selecting one of the first through M-th sets of parameter values that satisfies a condition; and (d) controlling the display unit to display a column of N pixels having first through N-th pixel values, each of the first through N-th pixel values being a function of the set of parameter values selected in operation (c).

* * * * *